US009211247B2

(12) United States Patent
Barrie et al.

(10) Patent No.: US 9,211,247 B2
(45) Date of Patent: Dec. 15, 2015

(54) SHELLAC BASED SPRAYABLE SUNSCREEN

(75) Inventors: William Barrie, Fairfield, CT (US);
Stephen A. Santos, Cumberland, RI (US)

(73) Assignee: Mantrose-Haeuser Company, Inc., Lincoln, RI (US)

( * ) Notice: Subject to any disclaimer, the term of this patent is extended or adjusted under 35 U.S.C. 154(b) by 0 days.

(21) Appl. No.: 14/344,635

(22) PCT Filed: Sep. 10, 2012

(86) PCT No.: PCT/US2012/054418
§ 371 (c)(1),
(2), (4) Date: Mar. 13, 2014

(87) PCT Pub. No.: WO2013/039826
PCT Pub. Date: Mar. 21, 2013

(65) Prior Publication Data
US 2014/0348757 A1    Nov. 27, 2014

Related U.S. Application Data

(60) Provisional application No. 61/534,144, filed on Sep. 13, 2011.

(51) Int. Cl.
| *A61K 8/04* | (2006.01) |
| *A61K 8/34* | (2006.01) |
| *A61K 8/92* | (2006.01) |
| *A61K 8/98* | (2006.01) |
| *A61Q 17/04* | (2006.01) |

(52) U.S. Cl.
CPC ............. *A61K 8/927* (2013.01); *A61K 8/046* (2013.01); *A61K 8/34* (2013.01); *A61K 8/988* (2013.01); *A61Q 17/04* (2013.01)

(58) Field of Classification Search
CPC ......... A61K 8/046; A61K 8/34; A61K 8/927; A61K 8/988; A61Q 17/04
See application file for complete search history.

(56) References Cited

U.S. PATENT DOCUMENTS

| 3,142,622 | A | | 7/1964 | Clapp |
| 4,910,197 | A | | 3/1990 | Beltner |
| 5,053,218 | A | * | 10/1991 | Shernov .................... 424/47 |
| 5,169,624 | A | | 12/1992 | Ziegler et al. |
| 5,543,136 | A | | 8/1996 | Aldous |
| 5,849,273 | A | | 12/1998 | Bonda et al. |
| 5,904,917 | A | | 5/1999 | Mattai et al. |
| 6,126,930 | A | | 10/2000 | Dubois et al. |
| 6,217,852 | B1 | | 4/2001 | Gildenberg et al. |
| 6,224,852 | B1 | | 5/2001 | Morgan et al. |
| 6,348,217 | B1 | | 2/2002 | Santos et al. |
| 7,226,581 | B2 | | 6/2007 | Traynor et al. |
| 2002/0164362 | A1 | | 11/2002 | Golz-Berner |
| 2004/0228810 | A1 | | 11/2004 | Hamson et al. |
| 2009/0004252 | A1 | | 1/2009 | Lowndes et al. |
| 2009/0035234 | A1 | | 2/2009 | Cunningham et al. |
| 2010/0297043 | A1 | * | 11/2010 | Lowndes ................. A61K 8/34 424/59 |

FOREIGN PATENT DOCUMENTS

WO    WO 2006/010222 A1 *    2/2006   ............. A61K 7/021

OTHER PUBLICATIONS

Search Report from European Patent Application No. EP12831671 dated Feb. 11, 2015.
International Search Report from International Application No. PCT/US12/54418 dated Nov. 2, 2012.
Federal Register, vol. 43, No. 166, pp. 38206-38269, Aug. 25, 1978.
First Office Action from Chinese Patent Application No. 201280044169.6 dated May 6, 2015.

* cited by examiner

*Primary Examiner* — Aradhana Sasan
(74) *Attorney, Agent, or Firm* — Calfee, Halter & Griswold, LLP

(57) ABSTRACT

A sprayable alcohol-based sunscreen comprises an alcohol carrier, at least one sunscreen additive, and a film forming polymer comprising shellac.

9 Claims, No Drawings

SHELLAC BASED SPRAYABLE SUNSCREEN

CROSS REFERENCE TO RELATED APPLICATIONS

This application is a 371 application of International Application No. PCT/US 2012/054418 with an international filing date of Sep. 10, 2012, which claims the benefit of U.S. Provisional Patent Application No. 61/534,144, filed on Sep. 13, 2011, the entire disclosures of which are incorporated herein by reference.

FIELD OF THE INVENTION

This invention relates to alcohol-containing sunscreen and other topical pharmaceutical compositions which are sprayable.

BACKGROUND

U.S. Pat. No. 6,126,930, the entire disclosure of which is incorporated herein by reference, describes sprayable sunscreen and other topical pharmaceutical compositions which contain a substantial amount of alcohol. Normally included in such compositions is a small but suitable amount of film forming polymer, which forms a protective coating to resist loss of the active ingredient through contact with water ("water resistance") or other physical contact ("rub-off resistance").

Increasingly popular products of this type are sprayable sunscreens. In addition to their alcohol carriers and film forming polymers, these products also contain sunscreen additives, i.e., compounds capable of absorbing or reflecting harmful radiation from the sun, as well as optional ingredients such as emollients, perfumes and the like.

Currently, the film forming polymers of choice in such products are acrylic based, especially acrylamide based polymers. This is because such polymers are not only readily soluble in alcohol but also provide a desirable tactile sensation. On the other hand, these polymers are not biodegradable as they are synthetic and petroleum based. In addition, they are not inexpensive. Accordingly, it would be desirable to provide new sprayable, alcohol based sunscreen compositions which are made with film forming polymers which are naturally-occurring, biodegrade, and less expensive than the acrylic polymers currently being used.

SUMMARY OF THE INVENTION

In accordance with this invention, it has been found that shellac, and especially dewaxed shellac, can serve as an excellent film forming polymer for use in making sprayable, alcohol-based topical pharmaceutical compositions, not only because shellac is readily soluble in alcohol but also because shellac provides essentially the same desirable tactile sensation as the acrylic and acrylamide polymers currently being used. In addition, because shellac is naturally occurring and not petroleum based, it is not only less expensive than acrylic based polymers but also biodegradable.

Thus, this invention provides a new sprayable alcohol-based topical pharmaceutical composition comprising an alcohol carrier, at least one pharmaceutical agent, and a film forming polymer capable of forming a protective coating on the skin to which the composition is applied, the film forming polymer comprising shellac.

In addition, this invention further provides a new product comprising a container, a sprayable alcohol-based topical pharmaceutical composition in the container, and a spray device for applying the composition in the container to a surface by spraying.

In addition, this invention also provides a new alcohol-based sprayable topical sunscreen comprising an alcohol carrier, at least one sunscreen additive, and a film forming polymer capable of forming a protective coating on the skin to which the sunscreen is applied, the film forming polymer comprising shellac.

In addition, this invention further provides a new technique for reducing the harmful effects of solar radiation on the skin, this new technique comprising applying the above sunscreen to the skin.

DETAILED DESCRIPTION

Basis Weight

Unless otherwise indicated, the concentrations of ingredients specified below are given in terms of the weight of the ingredient based on the weight of the inventive sprayable pharmaceutical composition as a whole but excluding any propellant that might be present.

In this connection, it should be understood that "pharmaceutical" is used in this document in its broadest sense to refer to any active ingredient likely to be found in a pharmacy. It is not used in its narrow sense as referring only to drugs. This is made clear by the fact that most sunscreens are not classified as drugs, since they work through absorption or blocking of the sun's harmful rays, not through a physiological effect.

Topical Pharmaceutical Compositions

This invention is applicable to making any type of sprayable, topical pharmaceutical composition which is alcohol-based. In this context, "topical" means that the composition is intended to be applied to the skin. Although the primary focus of this invention is on sunscreens, other sprayable, alcohol-based topical pharmaceutical compositions can also be made using the technology of this invention. Specific examples include pharmaceutical composition containing anti-acne agents, anti-wrinkle and anti-skin atrophy agents, non-steroidal anti-inflammatory actives, topical anesthetics, artificial tanning agents and accelerators, anti-microbial and antifungal actives, and various transdermal medicaments such as birth control medications, anti-smoking medications, and the like. Generally speaking, all of the different types and kinds of sprayable, alcohol-based topical pharmaceutical compositions described in the above-mentioned U.S. Pat. No. 6,126,930 can be made using the technology of this invention.

Sprayable Compositions

The inventive compositions are sprayable. This means that they can be sprayed or atomized as described in the above-mentioned U.S. Pat. No. 6,126,930. Thus, the inventive products can be delivered from non-aerosol mechanical pump spray devices or from pressurized aerosol canisters using a propellant or from any other mechanism or method of dispersing compositions for topical application to the skin. A wide range of mechanical pump spray devices and aerosol canister systems are well known to those of ordinary skill in the art. Similarly, a wide range of propellant materials are well known to those skilled in the art. Nonlimiting examples include lower molecular weight hydrocarbons such as propane n-butane and isobutane, nitrogen, carbon dioxide, nitrous oxide, and so forth. Mixtures of such propellants can also be used.

In those embodiments in which the inventive sprayable, topical pharmaceutical composition are supplied from pressurized aerosol canisters, the amount of propellant included in the composition may be as little as about 10 wt % to as much as about 75% propellant, based on the weight of the composition as a whole including the propellant. Propellant concentrations on the order of about 20 wt. % to about 50 wt % are more typical.

Alcohol Based

The inventive sprayable, topical pharmaceutical composition are alcohol-based. In this context, "alcohol-based" means that at least 50 wt. % of the liquid carrier of the composition, based on the weight of the liquid carrier, is composed of one or more alcohols. Normally, the inventive compositions contain at least about 40 wt. %, at least about 50 wt. % or even at least about 55 wt. % alcohol, based on the weight of the composition as a whole, excluding propellant. In addition, the inventive compositions typically contain no more than about 95 wt. %, no more than about 85 wt. %, no more than about 80 wt. %, or even no more than about 75 wt. %, alcohol, based on the weight of the composition as a whole, excluding propellant.

Any alcohol which has previously been used, or which may be used in the future, as a liquid carrier in a sprayable, topical pharmaceutical composition can be used as the alcohol in the inventive compositions. Thus, monohydric alcohols having 2 to 8 carbon atoms can be used. Specific examples include ethanol, n-propanol, iso-propanol, and mixtures thereof. Ethanol is preferred, especially denatured ethanol including any known cosmetically or pharmaceutically-acceptable denaturing agent. Specific commercially available alcohols which are useful for this purpose include SD (Specially Denatured) Alcohol 3-A, SD Alcohol 30, SD Alcohol 39, SD Alcohol 39-B, SD Alcohol 39-C, SD Alcohol 40, SD Alcohol 40-B, SD Alcohol 40-C. As well known, these designations have been assigned by the U.S. Bureau of Alcohol, Tobacco and. Firearms to refer to denatured ethanol compositions containing different amounts and types of common denaturants including denatonium benzoate, quassin, brucine and brucine sulfate.

Also, in some embodiments, the inventive sprayable, topical pharmaceutical composition are essentially free of water. This means that the amount of water in the composition is no more than is contributed by the 190 proof alcohol that is used to make the inventive compositions, i.e., a maximum water content of no more than about 2 wt. %. Maximum water contents of no more than about 1.0 wt. %, no more than about 0.5 wt. %, and even no more than about 0.1 wt. % are contemplated. In other embodiments, the inventive sprayable, topical pharmaceutical composition are entirely free of water.

Sunscreen Additives

As indicated above, the primary focus of this invention is on sunscreens. In this embodiment, the inventive compositions contains at least one sunscreen additive. In this context, a "sunscreen additive" is a compound or material which, when applied to the skin, is effective in reducing the amount of damaging solar radiation reaching the skin. Normally, this reduction occurs as a result of the sunscreen additive absorbing the harmful solar radiation. Other sunscreen additives work by reflecting harmful solar radiation. Such sunscreen additives are well known, and any compound or material which has previously been used for this purpose, or which is used for this purpose in the future, can be used as the sunscreen additive in the inventive compositions. In some embodiments, at least some of the sunscreen additives used are soluble in the alcohol carrier. In other embodiments, all of the sunscreen additives are soluble in the alcohol carrier.

In this regard, see U.S. Pat. No. 7,226,581, the entire disclosure of which is incorporated herein by reference, provides an extensive list of known sunscreen additives beginning at col. 6, line 11. As described there, organic sunscreens may be classified into five groups based upon their chemical structure: para-amino benzoates; salicylates; cinnamates; benzophenones; and miscellaneous chemicals including menthyl anthralinate and digalloyl trioleate. Inorganic sunscreens may also be used including titanium dioxide, zinc oxide, iron oxide and polymer particles such as those of polyethylene and polyamides. In accordance with this invention, each of these sunscreen additives, both organic and inorganic, as well as mixtures of two, three, four, five or more of these sunscreen additives, can be used to make the inventive sprayable sunscreen compositions.

Specific examples of suitable organic sunscreen additives include: p-aminobenzoic acid, its salts and its derivatives (ethyl, isobutyl, glyceryl esters; p-dimethylaminobenzoic acid); Anthranilates (i.e., o-aminobenzoates; methyl, menthyl, phenyl, benzyl, phenylethyl, linalyl, terpinyl, and cyclohexenyl esters); Salicylates (amyl, phenyl, benzyl, menthyl, glyceryl, and dipropylene glycol esters); Cinnamic acid derivatives (methyl and benzyl esters, alpha-phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naphtholsulfonates (sodium salts of 2-naphthol-3,3-disulfonic and of 2-naphthol-6,8-disulfonic acids); Dihydroxynaphthoic acid and its salts; o- and p-Hydroxybiphenyldisulfonates; Coumarin derivatives (7-hydroxy, 7-methyl, 3-phenlyll); Diazoles (2-acetyl-3-bromoindazole, phenyl benzoxazole, methyl naphthoxalole, various aryl benzothiazoles); Quinine salts (bisulfate, sulfate, chloride, oleate, and tannate); quinoline derivatives (8-hydroxyquinoline salts, 2-phenylquinoline); Hydroxy- or methoxy substituted benzophenones; Uric and viIouric acids; Tannic acid and its derivatives (e.g., hexaethylether); (Butyl carbityl) (6-propyl piperonyl) ether; Hydroquinone; Benzophenones (Oxybenzene, Sulisobenzone, Dioxybenzone, Benzoresorcinol, 2,2',4,4'-Tetrahydroxybenzophenone, 2,2'-Dihydroxy-4, 4'-dimethoxybenzophenone, Octabenzone; 4-Isopropyhldibenzoylmethane; Butylmethoxydibenzoylmethane; Etocrylene; and 4-isopropyl-di-benzoylmethane; titanium dioxide, iron oxide, zinc oxide, and mixtures thereof.

Other cosmetically-acceptable organic sunscreens and concentrations (percent by weight of the total cosmetic sunscreen composition) include diethanolamine methoxycinnamate (preferably 10% or less), ethy[bis(hydroxypropyl)] aminobenzoate (preferably 5% or less), glyceryl aminobenzoate (preferably 3% or less), 4-isopropyl dibenzoylmethane (5% or less), 4-methylbenzylidene camphor (preferably 6% or less), terephthalylidene dicamphor sulfonic acid (preferably 10% or less), and sulisobenzone (also called benzophenone-4, 10% or less).

In preferred embodiments, sunscreens are FDA-approved or approved for use in the European Union. For example, FDA-approved sunscreens may be used, singly or, preferably, in combination. See, e.g., U.S. Pat. Nos. 5,169,624; 5,543, 136; 5,849,273; 5,904,917; 6,224,852; 6,217,852; and Segarin et al., chapter Vil, pages 189 of Cosmetics Science and Technology, and Final Over-the-Counter Drug Products Monograph on Sunscreens (Federal Register, 1999:64: 27666-27963), all of which are incorporated herein by reference.

Thus, for products marketed in the United States, preferred cosmetically-acceptable organic sunscreens and concentrations include: aminobenzoic acid (also called para-aminobenzoic acid and PABA; preferably 15% or less; a UVB absorbing organic sunscreen), avobenzone (also called butyl methoxy dibenzoylmethane; preferably 3% or less, a UVA absorbing organic sunscreen), cinoxate (also called 2-ethoxyethyl p-methoxycinnamate; preferably 3% or less, a UVB absorbing organic sunscreen), dioxybenzone (also called benzophenone-8; preferably 3% or less, a UVB and UVA II absorbing organic sunscreen), homosalate (preferably 15% or less, a UVB absorbing organic sunscreen), menthyl anthranilate (also called menthyl 2-aminobenzoate; preferably 5% or less, a UVA II absorbing organic sunscreen), octocrylene (also called 2-ethylhexyl-2-cyano-3,3 diphenylacrylate; 10% or less, a UVB absorbing organic sunscreen), octyl methoxycinnamate (preferably 7.5% or less, a UVB absorbing organic sunscreen), octyl salicylate (also called 2-ethylhexyl salicylate; preferably 5% or less, a UVB absorbing organic sunscreen), oxybenzone (also called benzophenone-3; preferably 6% or less, a UVB and UVA H absorbing organic sunscreen), padimate O (also called octyl dimethyl PABA; preferably 8% or less, a UVB absorbing organic sunscreen), phenylbenzimidazole sulfonic acid (water soluble; preferably 4% or less, a UVB absorbing organic sunscreen), sulisobenzone (also called benzophenone-4; preferably 10% or less, a UVB and UVA II absorbing organic sunscreen), titanium dioxide (preferably 25% or less, an inorganic physical blocker of UVA and UVB), trolamine salicylate (also called triethanolamine salicylate; preferably 12% or less, a UVB absorbing organic sunscreen), and zinc oxide (preferably 25% or less, an inorganic physical blocker of UVA and UVB).

For products marketed in the European Union, preferred cosmetically-acceptable organic photoactive compounds and concentrations include: PABA (preferably 5% or less), camphor benzalkonium methosulfate (preferably 6% or less), homosalate (preferably 10% or less), benzophenone-3 (preferably 10% or less), phenylbenzimidazole sulfonic acid (preferably 8% or less, expressed as acid), terephthalidene dicamphor sulfonic acid (preferably 10% or less, expressed as acid), butyl methoxydibenzoylmethane (preferably 5% or less), benzylidene camphor sulfonic acid (preferably 6% or less, expressed as acid), octocrylene (preferably 10% or less, expressed as acid), polyacrylamidomethyl benzylidene camphor (preferably 6% or less), octyl methoxycinnamate (preferably 10% or less), PEG-25 PABA (preferably 10% or less), isoamyl p-methoxycinnamate (preferably 10% or less), ethylhexyl triazone (preferably 5% or less), drometrizole trielloxane (preferably 15% or less), diethylhexyl butamido triazone (preferably 10% or less), 4-methylbenzylidene camphor (preferably 4% or less), 3-benzylidene camphor (preferably 2% or less), ethylhexyl salicylate (preferably 5% or less), ethylhexyl dimethyl PABA (preferably 8% or less), benzophenone-4 (5%, expressed as acid), methylene bis-benztriazolyl tetramethylbutylphenol (preferably 10% or less), disodium phenyl dibenzimidazole tetrasulfonate (preferably 10% or less, expressed as acid), bis-ethylhexyloxyphenol methoxyphenol triazine (preferably 10% or less), methylene bisbenzotriazolyl tetramethylbutylphenol (preferably 10% or less, also called TINOSORB M), and bisethylhexyloxyphenol methoxyphenyl triazine (preferably 10% or less, also called TINOSORB S).

The amount of sunscreen additive which included in the inventive sprayable sunscreen depends on the particular sunscreen additive or additives that are used as well as the desired Sun Protection Factor (SPF) of the composition. SPF is a commonly used measure of photoprotection of a sunscreen against erythema. See Federal Register VoL 43, No. 166, pp. 38206-38269, Aug. 25, 1978, which is incorporated herein by reference in its entirety.

Minimum sunscreen additive concentrations of about 0.1 wt. % or less are contemplated as are maximum concentrations of 50 wt. % or more. More typically, the inventive sprayable sunscreen will contain at least about 5 wt. %, at least about 10 wt. %, at least about 15 wt. %, or even at least about 20 wt. %, sunscreen additive depending on the type of sunscreen additive used and the SPF desired. In the same way, the inventive sprayable sunscreen will typically contain no more than about 50 wt. %, no more than about 45 wt. %, no more than about 40 wt. %, or no more than about 35 wt. %, sunscreen additive depending on the type of sunscreen additive used and the SPF desired.

Emollients

The inventive sprayable pharmaceutical compostions may also contain a water-insoluble liquid emollient such as fatty acids such as oleic and recinoleic; fatty alcohols such as oleyl, lauryl, and hexadecyl (ENJAY); esters such as diisopropyl adipate, benzoic acid esters of $C_9$-$C_{15}$ alcohols, and isononyl iso-nonanoate; alkanes such as mineral oil; alkenes such as polybutenes; silicones; such as dimethylpolysiloxane and methyl phenyl polysiloxane and ethers such as polyoxypropylene butyl ethers and polyoxpropylene cetyl ethers. The most preferred water-insoluble liquid emollients are: polybutene 30 cst., methyl phenyl polysiloxane, dimethylpolysiloxane 5.0 cst. and polyoxypropylene (14) butyl ether. The amount of water-insoluble liquid emollient is form about 2% to about 15% by weight, preferably from about 4% to about 10%.

The water-insoluble liquid emollient can be used to decrease any drying effect to the skin attributed by the monohydric alcohol and also to control the rate of product depositing on the skin. One skilled in the art will easily be able to adjust the cosmetic aesthetics and physical characteristics of the composition by combining various amounts of suitable water-insoluble liquid emollients.

Other Conventional Ingredients

In addition, the inventive sprayable alcohol-based topical pharmaceutical compositions can contain any other ingredient which is conventionally included in similar compositions. Examples include perfumes, deodorant compounds, astringent salts, antioxidants, insect repellants and so forth Shellac Film Former In accordance with this invention, shellac is used as the film former in the inventive sprayable alcohol-based topical pharmaceutical compositions. Preferably, a dewaxed shellac is used.

Shellac is a naturally occurring thermoplastic obtained from secretions of the female lac bug. It exhibits a remarkable combination of properties including low permeabilities to oxygen, water vapor, $CO_2$, ethylene and various odors, low lipid solubility, excellent color and excellent clarity.

Shellac is obtained from seedlac, an insect secretion, by removing debris from the seedlac and then further processing the seedlac to obtain the desired product. Commercially, shellac is available in two different types, bleached shellac and orange shellac. Moreover, both of these shellacs are available in refined (i.e., dewaxed) as well as unrefined (regular) versions. In addition, each of these four different varieties of shellac are available in different physical forms, e.g., solid flakes and aqueous and/or alcohol solutions. In addition, some of these different varieties are also available in different grades. For example, dewaxed orange shellac is available in a variety of different grades ranging from faint orange to intense orangish red.

As described in U.S. Pat. No. 6,348,217, the entire disclosure of which is incorporated herein by reference, bleached shellac is made by dissolving seedlac in aqueous alkali and then adding a bleaching agent such as sodium hypochlorite. The product so obtained is then precipitated and dried to produce regular bleached shellac. Alternatively, the dissolved bleached shellac can be refined by known techniques to remove its wax content before precipitating and drying, thereby producing dewaxed bleached shellac. In contrast, regular orange shellac is made by melting seedlac, sieving out the insolubles and then solidifying and flaking the product so obtained. Meanwhile, dewaxed orange shellac is made by dissolving the seedlac in alcohol, straining out the insolubles, filtering out wax particles and passing the solution so obtained through activated carbon to decolorize before solidifying and flaking.

In accordance with this invention, each of these different types of shellac can be used as the film forming polymer in the inventive sprayable pharmaceutical compositions. Shellac is readily soluble in alcohol, especially ethanol, and so it easily forms sprayable compositions with the other ingredients found in a typical sprayable alcohol-based topical pharmaceutical composition. However, because shellac is naturally-occurring, it is readily biodegradable in contrast to the acrylic and acrylamide polymers which are currently used as film formers, which are synthetic derivatives of petroleum. In addition, shellac is less expensive than these synthetic polymers. More importantly, it has also been found in accordance with this invention that shellac and especially dewaxed shellac exhibits a tactile sensation when applied to the skin, both while still wet as well as after being dried, that is essentially the same as that exhibited by these conventional acrylic and acrylamide polymers.

So, for example, the inventive compositions, like sprayable sunscreens made with conventional film formers, exhibit an initial oil-watery feel and absorb quickly with little or no stick/tack feel and no cooling feeling. In addition, like conventional compositions, the amount of residue produced by the inventive compositions is low and decreases over 10 minutes, leaving a feel that is mostly waxy and plastic-like without being sticky/tacky or causing a draggy feeling on the skin. In addition, like conventional compositions, the inventive compositions exhibit no peeling, flaking, beading or pilling.

Most importantly, in sunscreens, shellac has also been found just as effective as the conventional acrylic and acrylamide-based film formers in terms of preventing wash off and rub off without adversely affecting SPF values.

Accordingly, shellac makes an excellent replacement for the acrylic and acrylamide polymers which are currently used as the film formers in conventional sprayable alcohol-based topical pharmaceutical compositions, because it exhibits essentially the same performance as these synthetic polymers but is naturally-occurring, biodegradable and less expensive.

The amount of shellac film former that is included in the inventive sprayable alcohol-based topical pharmaceutical compositions is generally the same as the amount of conventional acrylic or acrylamide based film formers used in conventional alcohol-based topical pharmaceutical compositions. So, for example, the inventive compositions can contain as little as 0.5 wt % or less shellac, although minimum shellac concentrations of about 1.0 wt %, about 1.5 wt % or even 2.0 wt % are more common. Similarly, the inventive compositions can contain as much as 10 wt % or more shellac, although maximum shellac concentrations of about 7.0 wt %, about 5.0 wt % or even 3.0 wt % are more common.

EXAMPLES

In order to more thoroughly illustrate this invention, the following working examples are presented. Three different samples were tested, a comparative sample using a conventional acrylic based polymer as the film former (Dermacryl 79) and two samples representing this invention using a dewaxed bleached shellac and a dewaxed orange shellac as the film former in the same amount. All other ingredients of all three compositions were the same.

In each of these examples, 2.50 wt % film forming polymer was mixed with 63.50 wt. % SD alcohol 40 (denatured alcohol) until the film former was dissolved, which took about 20 minutes to 2 hours depending on the particular film former used. Separately, 5.00 wt % ethylhexyl salicylate (octisalate) (sunscreen additive), 3.00 wt. % butyl methoxydibenzoylmethane (avobenzone) (sunscreen additive), 3.00 wt. % octocrylene (sunscreen additive), 6.00 wt. % butyl salicylate (sunscreen additive/stabilizer/emollient), 5.00 wt. % oxybenzone (sunscreen) and 10.00 wt. % homosalate (sunscreen) were combined and mixed at 60° C. until all ingredients were dissolved. The two compositions were then combined and mixed until a uniform mixture was obtained, after which the mixture was cooled to 40° to 45° C. to produce the sunscreen composition.

Each sunscreen so made was then subjected to a tactile and appearance descriptive analysis on dry and wet skin by applying each sunscreen composition to a 2 inch by 4 inch test site of each member of a trained skinfeel descriptive analysis panel composed of nine different individuals. For this purpose, four different observations were taken, one while the skin was still wet, one immediately after the sunscreens had dried, another two minutes later and the last 10 minutes later. In addition, a separate SPF analysis was conducted on a panel of five individuals composed of one female and four male subjects to determine the effectiveness of these sunscreen compositions in terms of blocking harmful solar radiation.

All three sunscreens exhibited an SPF value of about 51.4 to 53.5, thereby demonstrating that dewaxed bleach shellac and dewaxed orange shellac perform just as effectively as Dermacryl 79 in terms of not reducing the effectiveness of the sunscreen additives in these sunscreen compositions. In addition, the tactile and appearance descriptive analyses show that the two inventive sunscreens performed essentially the same as the conventional sunscreen in terms of skin feel. This demonstrates that shellac performs essentially the same as the conventional film formers used in conventional spray on alcohol based sunscreens even though shellac is a less expensive, naturally occurring biodegradable product.

Although only a few embodiments of this invention have been described above, it should be appreciated that many modifications can be made without departing from the spirit and scope of this invention. All such modifications are intended to be included within the scope of this invention, which is to be limited only by the following claims:

The invention claimed is:

1. A sprayable sunscreen composition which forms a protective skin coating essentially free of stickiness and tack, the sunscreen composition consisting essentially of at least 50 wt. % of an alcohol carrier, about 10-45 wt. % of one or more organic sunscreen additives, and about 1 to 5 wt. % of shellac, these percents being based on the weight of sunscreen composition as a whole but excluding any propellant that might also be present, wherein all of the sunscreen additives and all of the shellac are dissolved in the alcohol carrier.

2. The sunscreen composition of claim 1, wherein the sunscreen contains about 20-45 wt. % of one or more organic sunscreen additives.

3. The sunscreen composition of claim 2, wherein the sunscreen additives are selected from the group consisting of para-amino benzoates, salicylates, cinnamates, benzophenones, menthyl anthralinate and digalloyl trioleate.

4. The sunscreen composition of claim 3, wherein the sunscreen contains about 2-3 wt. % shellac.

5. The sunscreen composition of claim 4, wherein all of the ingredients in the sunscreen other than the alcohol carrier are dissolved in the alcohol carrier.

6. The sunscreen composition of claim 1, wherein the sunscreen contains about 20-45 wt. % of one or more organic sunscreen additives selected from the group consisting of para-amino benzoates, salicylates, cinnamates, benzophenones, menthyl anthralinate and digalloyl trioleate and further wherein all of the ingredients in the sunscreen other than the alcohol carrier are dissolved in the alcohol carrier.

7. The sunscreen composition of claim 6, wherein the sunscreen contains about 2-3 wt. % shellac.

8. The sunscreen composition of claim 1, wherein the composition contains a preservative.

9. A process for reducing the harmful effects of solar radiation on the skin, the process comprising applying the sunscreen of claim 1 to the skin.

\* \* \* \* \*